US006194587B1

(12) United States Patent
Doshi

(10) Patent No.: US 6,194,587 B1
(45) Date of Patent: Feb. 27, 2001

(54) PRODUCTION OF MALEIC ANHYDRIDE

(75) Inventor: Bharat M. Doshi, Piscataway, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

(21) Appl. No.: 09/377,589

(22) Filed: Aug. 19, 1999

(51) Int. Cl.[7] .................................................. C07D 307/60
(52) U.S. Cl. ............................................ 549/258; 549/259
(58) Field of Search ...................................... 549/259, 258

(56) References Cited

U.S. PATENT DOCUMENTS 5,360,916   11/1994   Padia et al. ........................... 549/259
5,885,919   3/1999   Bortinger ............................. 502/209

OTHER PUBLICATIONS

T.C. Bissot et al "Oxidation of Butane to Maleic Anhydride", IEC vol 2 No 1 3/63 p. 57–60.

Primary Examiner—Bernard Dentz
(74) Attorney, Agent, or Firm—William C. Long

(57) ABSTRACT

N-butane and molecular oxygen are reacted in a first reactor to form maleic anhydride, the produced maleic anhydride is scrubbed to separate maleic anhydride values, n-butane is added to the scrubber gases and these are reacted in a second reactor to form additional maleic anhydride.

6 Claims, 1 Drawing Sheet

PRODUCTION OF MALEIC ANHYDRIDE

BACKGROUND OF THE INVENTION

1. Field of the Invention

The present invention relates to an improved process for the oxidation of n-butane to maleic anhydride. The specific improvement of the present invention resides in the use of a series of reactors to accomplish the n-butane oxidation with removal of product maleic anhydride from the effluent of a reactor prior to forwarding the remaining gases together with supplemental n-butane to the next in the series of oxidation reactors. Air or oxygen enriched air can be used to accomplish the oxidation.

2. Description of the Prior Art

The production of maleic anhydride by the oxidation of n-butane is, of course, by now a well known and commercially practiced process. Primarily the maleic anhydride is produced by introducing n-butane in admixture with air into contact with an oxidation catalyst such as a VPO catalyst under conditions such that the n-butane is oxidized to maleic anhydride. In conventional practices, the effluent from this reactor may be cooled to partially condense the product maleic anhydride from the effluent gases. The gaseous product, with or without partial maleic anhydride removal, is scrubbed using a solvent, usually water, to recover all of product maleic anhydride. The remaining gases, containing unconverted n-butane, are commonly incinerated in an effluent gas incinerator prior to venting to atmosphere.

There are references which relate to the use of more than one reactor in series in order to produce maleic anhydride. Specifically, U.S. Pat. No. 5,360,916 provides a two stage process for maleic anhydride production wherein n-butane is oxidized in a first reaction zone and the effluent from this zone is passed together with supplemental n-butane to a second reactor in series in order to complete production of the maleic anhydride. A feature of the process described in this patent is that there is at most only a partial removal of maleic anhydride by condensation from the effluent from the first of the reactors prior to introduction into the second and last in the series of reactors.

A literature article by Bissot et al. entitled "Oxidation of Butane to Malic Anhydride" appearing in IEC vol. 2 No. 1 March 1963, pages 57–60 discloses a process for maleic anhydride production wherein n-butane is oxidized in a series of fluidized bed reactors using a cobalt or nickel molybdate catalyst, the effluent from the first of the reactors passing to the second reactor after intermediate removal of product maleic anhydride. There is no teaching in this literature reference of the addition of supplemental n-butane to the effluent of the first of the reactors prior to continuing the reaction in a second reactor after maleic anhydride removal.

BRIEF DESCRIPTION OF THE INVENTION

In accordance with the present invention, n-butane is oxidized using a VPO catalyst in a first reactor, preferably a fixed bed reactor, in order to produce maleic anhydride. This reaction is carried out in accordance with known procedures. The effluent from this first reactor is cooled and either optionally treated for partial condensation of product maleic anhydride by cooling and/or directly scrubbed with liquid, preferably water, to separate all of the remaining maleic anhydride formed in the first reactor. The gases from the scrubber which comprise unreacted n-butane and unreacted oxygen, are passed together with supplemental added n-butane to a second reactor, preferably a similar fixed bed reactor, wherein the reaction is continued converting n-butane to additional product maleic anhydride. The effluent from the second reactor is then treated in accordance with conventional procedures to recover the product maleic anhydride values. Where more than two reactors are employed, the scrubber gases are further treated as above described; that is oxidized to maleic anhydride after addition of supplemental n-butane.

BRIEF DESCRIPTION OF THE DRAWINGS

The accompanying FIGURE illustrates in schematic form a suitable practice of the present invention.

DETAILED DESCRIPTION

Figure 1:
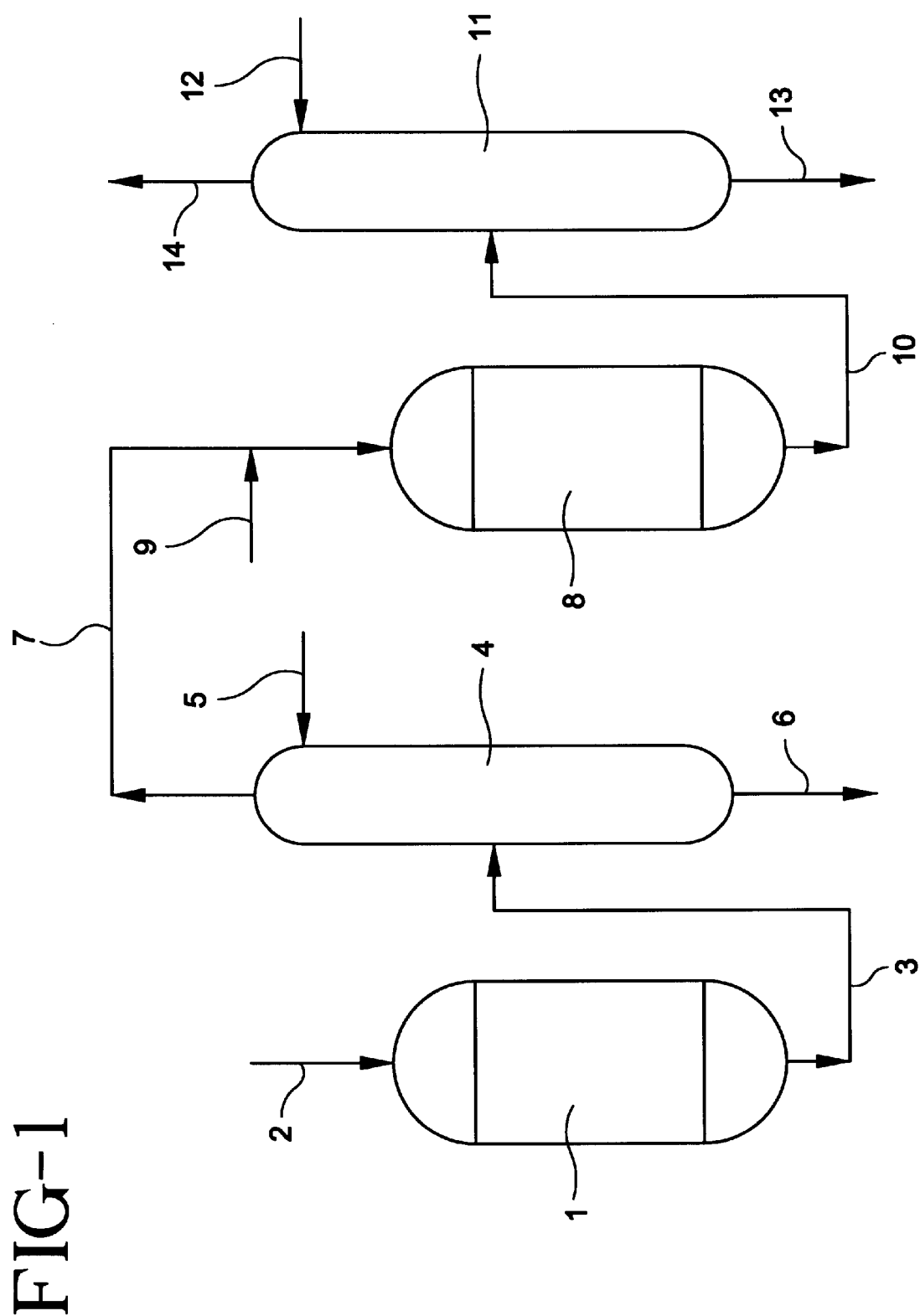

In accordance with the present invention, n-butane together with a molecular oxygen containing gas such as air or oxygen enriched air is introduced into a first reaction zone and therein the n-butane is oxidized by conventional procedures using a VPO catalyst to produce maleic anhydride. The gaseous effluent from this first reactor is then passed to a first scrubbing zone, optionally after part of the maleic anhydride is removed by partial condensation, wherein product maleic anhydride formed in the first reactor is scrubbed from these effluent gases and comprises a product of the process; some of the water of reaction is also removed in the scrubbing zone. The gases from the scrubber comprised of some unreacted n-butane, unreacted oxygen, carbon monoxide, carbon dioxide, nitrogen and the like are then passed to a second reactor and therein further reacted to form additional maleic anhydride. Prior to introduction of this gas stream into the second reactor, supplemental n-butane is added to the feed in order to obtain a n-butane enriched feed stream to the second reactor. In the second reactor the gas mixture is oxidized using a VPO catalyst to produce additional maleic anhydride. Effluent from the second reactor after removal of all product maleic anhydride in the second scrubber can, if economical, be passed to a still further series reactor together with supplemental n-butane or the gases from the second reactor may be incinerated prior to discharge to the atmosphere.

A striking advantage of the present invention is the fact that operating costs including raw material costs and power costs are substantially reduced. Maleic anhydride production as a function of the capital needed for construction of a new maleic anhydride installation can be significantly reduced in accordance with the present invention. Thus, economies are effected in the compressor, scrubber, and other elements of equipment and lower operating costs are incurred in the production of the desired maleic anhydride. A main advantage in capital cost saving comes from a reduction in the size of the vent gas incinerator.

The accompanying drawing illustrates a preferred practice of the present invention.

Referring to the drawing, reactor 1 is a conventional multi tube fixed bed reactor packed with VPO catalyst suitable for the oxidation of n-butane to maleic anhydride in accordance with known procedures. A gas mixture comprised of n-butane and molecular oxygen (illustratively introduced as air) passes via line 2 to reactor 1 and is distributed to the various reactor tubes located therein. These tubes are surrounded by a circulating heat removal medium such as molten salt in accordance with known procedures. In passing through reactor 1 n-butane is reacted with the molecular oxygen under conditions effective to produce maleic anhydride.

The reaction mixture exits reactor 1 via line 3 and passes to scrubber 4. Scrubbing water is introduced into scrubber 4 by means of line 5 and in the scrubber maleic anhydride is effectively scrubbed from the mixture of reaction gases from reactor 1. An aqueous stream containing the scrubbed maleic anhydride, now in the form of maleic acid, exits scrubber 4 via line 6 and passes to refining wherein maleic anhydride is recovered by known procedures.

As an important feature of the present invention, the scrubbed gases from scrubber 4 exit via line 7 and pass to a second reactor, reactor 8, which can be similar to reactor 1 and indeed preferably contains the same VPO catalyst which is contained in reactor 1. As a critical feature of the present invention, supplemental n-butane is added to the exit gases from scrubber 4 via line 9, and this combination of gases is introduced as feed into reactor 8 and therein reacted under conditions effective for the oxidation of n-butane to maleic anhydride in accordance with known procedures.

Reaction gases from reactor 8 exit via line 10 and pass to scrubber 11 wherein these gases are contacted with scrubbing water which is introduced via line 12. Additional product maleic anhydride values are recovered in the aqueous stream removed from scrubber 11 via line 13. This stream may be combined with the stream from line 6 and together passed to a refining section wherein by conventional procedures maleic anhydride product is recovered.

Gases from scrubber 11 exit via line 14, these gases comprising a small amount of unreacted n-butane, which can be incinerated, together with unreacted oxygen in minor amount, nitrogen, and various carbon oxides together with various amounts of water. These gases are disposed of in accordance with known procedures.

An important advantage of practice of the present invention when compared to conventional single reactor procedures is that, for the two reactors in series, for the same maleic anhydride production the air feed rate and the vent gas load are cut almost in half. Overall n-butane consumption is substantially reduced, by as much as 10%, the power required in the air compressor is reduced by as much as 20% and the operating costs of a vent gas incinerator associated with the process is reduced by almost half. In addition, the capital cost of this vent gas incinerator is reduced substantially.

N-butane consumption is reduced largely because the n-butane contained in the gases exiting the first reactor rather then being flared or incinerated is fed to the second reactor. The advantages of this procedure are partially offset by a somewhat lower selectivity in the second stage reactor due to a less favorable inlet gas composition but on balance the advantages achieved through practice of the present invention result in up to 10% reduction in n-butane consumption for the same maleic anhydride production.

The same or different catalysts of the VPO type can be used in the several reactors; preferably the same catalyst is employed in each reactor. An especially useful catalyst is that described in U.S. Pat. No. 5,885,919 although practice of the invention is not restricted to the use of any particular catalyst.

The oxidation of the n-butane to maleic anhydride in each reactor is accomplished by contacting n-butane in low concentrations in oxygen with the described catalyst. Air is entirely satisfactory as a source of oxygen for the first reactor but synthetic mixtures of oxygen and diluent gases, such as nitrogen also may be employed. Air enriched with oxygen may be employed.

The gaseous feed stream to the first reactor normally will contain air and about 0.5 to about 3.0 mole percent n-butane. About 1.0 to about 2.5 mole percent of n-butane are satisfactory for optimum yield of product for the process of this invention. Although higher concentrations may be employed, explosion hazards may be encountered except in fluidized bed reactors where concentrations of up to about 4 or 5 mole percent can be used without explosive hazard. Lower concentrations of n-butane, less than about one percent, of course, will reduce the total productivity obtained at equivalent flow rates and thus are not normally economically employed.

The flow rate of the gaseous stream through the first reactor may be varied within rather wide limits but a preferred range of operations is at the rate of about 10 to 300 grams of n-butane per liter of catalyst per hour and more preferably about 50 to about 250 grams of n-butane per liter of catalyst per hour. Residence times of the gas stream will normally be less than about 4 seconds, more preferably less than about one second, and down to a rate where less efficient operations are obtained.

The temperature of reaction in the first reactor may be varied within some limits, but normally the reaction should be conducted at temperatures within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than about 100° C. above the salt bath temperature. The temperature in the reactor tubes, of course, will also depend to some extent upon the size of the tubes and the n-butane concentration. Under usual operating conditions in a preferred procedure, the temperature in the center of the reactor, measured by thermocouple, is about 365° to about 550° C. The range of temperature preferably employed in the reactor, measured as above, should be from about 380° C. to about 515° C. and the best results are ordinarily obtained at temperatures from about 380° C. to about 475° C. Described another way, in terms of salt bath reactors with carbon steel reactor tubes about 1.0" in diameter, the salt bath temperature will usually be controlled between about 350° C. to about 550° C. Under normal conditions, the temperature in the reactor ordinarily should not be allowed to go above about 475° C. for extended lengths of time because of decreased yields and possible deactivation of the catalyst.

The reaction may be conducted at atmospheric, super atmospheric or below atmospheric pressure. The exit pressure will be at least slightly higher than the ambient pressure to insure a positive flow from the reaction. The pressure of the gases must be sufficiently high to overcome the pressure drop through the reactor.

In accordance with the invention, the gaseous effluent exiting the first reactor is scrubbed with water optionally after separation of some maleic an hydride by cooling and condensation in order to separate essentially all product maleic anhydride values leaving a gas mixture containing substantial unreacted n-butane and molecular oxygen values. Generally this gas mixture comprises by volume about 0.1 to 1.0 vol %, the n-butane, preferably 0.2 to 0.6 vol %, the remainder being oxygen, nitrogen, carbon oxides, and the like. Typically the gas mixture comprises about 0.4 vol % n-butane.

N-butane is added to the gas mixture in amount generally sufficient to provide a combined gas mixture comprised by volume of 0.5 to 3.0 vol % n-butane and usually about 10 to 15 vol % molecular oxygen depending upon oxygen consumption in the first reactor. This mixture forms the feed to the second of the series of reactors.

The second reactor is similar to the first reactor, preferably containing the same VPO catalyst. Reaction conditions are much the same in the second reactor as in the first, and the reaction gas mixture exiting the second reactor is scrubbed with water to recover the additional maleic anhydride values, optionally after first cooling and condensing some maleic anhydride values. N-butane in the scrubber gases can be incinerated in a vent gas incinerator and vented to atmosphere or otherwise treated.

A variety of reactors will be found to be useful and multiple tube heat exchanger type reactors are quite satisfactory for each reactor. The tubes of such reactors may vary in diameter from about ¼" to about 3", and the length may be varied from about 3 to 18' or longer. The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Such media may be Woods metal, molten sulfur, mercury, molten lead, and the like, but it has been found that eutectic salt baths are completely satisfactory. One such salt bath is a sodium nitrate-sodium nitrite-potassium nitrite eutectic constant temperature mixture. An additional method of temperature control is to use a metal block reactor whereby the metal surrounding the tube acts as a temperature regulating body. As will be recognized by one skilled in the art, the heat exchange medium may be kept at the proper temperature by heat exchangers and the like. The reactor or reaction tubes may be iron, stainless steel, carbon steel or nickel and have excellent long life under the conditions for the reactions described herein. Normally, the reactors contain a preheat zone of an inert material such as ¼' Alundum pellets, inert ceramic balls, nickel balls or chips and the like, present at about ⅕ to 1/20 the volume of the active catalyst present.

EXAMPLE 1

A two series reactor system, as illustrated in the attached Figure, is provided for the oxidation of n-butane to maleic anhydride.

With reference to the Figure, n-butane together with air is fed via line 2 to reactor 1 and therein reacted to form maleic anhydride. Reactor 1 is a conventional multi tube reactor packed with VPO catalyst such as that described in Example 1 of U.S. Pat. No. 5,885,919 and provided with a coolant to remove reaction heat.

The feed enters reactor 1 and therein reacts to form maleic anhydride, the hot spot in the tubes is maintained at about 420–460° C., the gas feed is fed at 40–50 psia.

The reaction mixture exits reactor 1 via line 3 and is cooled in stages to about 60° C. (not shown). The cooled mixture is introduced into scrubber 4 and therein contacted with scrubbing water which is introduced via line 5. The aqueous stream containing the scrubbed maleic anhydride values is removed via line 6 and sent to conventional maleic anhydride recovery.

The reaction gas mixture from which maleic anhydride has been scrubbed is removed from scrubber 4 via line 7. Supplemental n-butane is added via line 9 and the resulting admixture is fed to reactor 8.

Reactor 8, like reactor 1, is a conventional multi tube reactor packed with the same VPO catalyst used in reactor 1. Hot spot temperature in reactor 8 is 420–460° C. and inlet pressure is about 30–40 psia.

The reaction gas mixture is removed from reactor 8 via line 10, cooled (not shown), and passed to scrubber 11 wherein maleic anhydride values are scrubbed with water which is introduced via line 12.

The scrubber liquid containing maleic anhydride formed in reactor 8 is removed from scrubber 11 via line 13 and sent to conventional maleic anhydride recovery.

Reaction gases are removed from scrubber 11 via line 14 and sent to a vent gas incinerator prior to venting to the atmosphere.

The following Table 1 gives the amounts and compositions of the various process streams. Table 2 gives the various conversions and selectivities.

TABLE 1

| Stream No. | 2 | | 3 | | 7 | |
|---|---|---|---|---|---|---|
| Component | Mols/hr | Mol % | Mols/hr | Mol % | Mols/hr | Mol % |
| n-butane | 56.23 | 1.9200 | 10.12 | 0.3389 | 10.12 | 0.3618 |
| iso-butane | 2.34 | 0.0800 | | 0.0000 | | 0.0000 |
| MAN | | | 32.56 | 1.0933 | | |
| CO | | | 36.58 | 1.2247 | 36.58 | 1.3074 |
| $CO_2$ | | | 26.13 | 0.8748 | 26.13 | 0.9339 |
| $O_2$ | 586.80 | 20.0283 | 388.43 | 13.0045 | 388.43 | 13.8829 |
| $N_2$ | 2213.41 | 75.5717 | 2213.53 | 74.1078 | 2213.53 | 79.1136 |
| $H_2O$ | 70.29 | 2.4000 | 279.45 | 9.3560 | 123.12 | 4.4004 |
| Total | 2928.89 | 100 | 2980.90 | 100 | 2797.91 | 100 |

| Stream No. | 9 | | 10 | | 14 | |
|---|---|---|---|---|---|---|
| Component | Mols/hr | Mol % | Mols/hr | Mol % | Mols/hr | Mol % |
| n-butane | 45.68 | 96.0000 | 11.01 | 0.3795 | 11.01 | 0.3975 |
| iso-butane | 1.90 | 4.0000 | | | | |
| MAN | | | 31.08 | 1.0715 | | |
| CO | | | 71.89 | 2.4784 | 71.89 | 2.5975 |
| $CO_2$ | | | 51.35 | 1.7703 | 51.35 | 1.8541 |
| $O_2$ | | | 199.80 | 6.8880 | 199.80 | 7.2104 |
| $N_2$ | | | 2214.02 | 78.3266 | 2214.02 | 79.9387 |
| $H_2O$ | | | 321.56 | 11.0856 | 221.57 | 8.0000 |
| Total | 47.59 | 100 | 2900.71 | 100 | 2769.64 | 100 |

TABLE 2

Basis Production of 63.74 mols/hr MAN
(equivalent to 6250 kg/hr of Product MAN)

| | REACTOR 1 | REACTOR 2 | OVERALL for the Plant |
|---|---|---|---|
| Total n-butane Mol % | 2.00 | 2.00 | 3.57 |
| n-butane Purity % | 96.00 | 96.70 | 96.00 |
| Conc. n-butane | 1.92 | 1.93 | 3.42 |
| Conc. iso-butane | 0.08 | 0.06 | 0.14 |
| Conv. n-butane | 82.00 | 80.00 | 89.05 |
| Conv. iso-butane | 100.00 | 100.00 | 100.00 |
| Overall Conv % | 82.72 | 80.86 | 89.49 |
| Selectivity % | 70.81 | 69.62 | 69.89 |
| RX Yield, wt. % | 98.00 | 94.00 | 105.54 |

EXAMPLE 2

This example illustrates practice of the invention using oxygen enriched air as the molecular oxygen containing gas in the first reactor in the two series reactor system as shown in the accompanying Figure.

With reference to the Figure, n-butane together with air enriched with oxygen to an oxygen concentration of 28 vol % (dry basis) is fed via line 2 to reactor 1 and therein reacted to form maleic anhydride. Reactor 1 is a conventional multi tube reactor packed with VPO catalyst such as that described in Example 1 of U.S. Pat. No. 5,885,919 and provided with a coolant to remove reaction heat.

The feed enters reactor 1 and therein reacts to form maleic anhydride, the hot spot in the tubes is maintained at about 420–460° C., the gas feed is fed at 40–50 psia.

The reaction mixture exits reactor 1 via line 3 and is cooled in stages to about 60° C. (not shown). The cooled mixture is introduced into scrubber 4 and therein contacted with scrubbing water which is introduced via line 5. The aqueous stream containing the scrubbed maleic anhydride values is removed via line 6 and sent to conventional maleic anhydride recovery.

The reaction gas mixture from which maleic anhydride has been scrubbed is removed from scrubber 4 via line 7. Supplemental n-butane is added via line 9 and the resulting admixture is fed to reactor 8.

Reactor 8, like reactor 1, is a conventional multi tube reactor packed with the same VPO catalyst used in reactor 1. Hot spot temperature in reactor 8 is 420–460° C. and inlet pressure is about 30–40 psia.

The reaction gas mixture is removed from reactor 8 via line 10, cooled (not shown), and passed to scrubber 11 wherein maleic anhydride values are scrubbed with water which is introduced via line 12.

The scrubber liquid containing maleic anhydride formed in reactor 8 is removed from scrubber 11 via line 13 and sent to conventional maleic anhydride recovery.

Reaction gases are removed from scrubber 11 via line 14 and sent to a vent gas incinerator prior to venting to the atmosphere.

The following Table 3 gives the amount and compositions of the various process streams. Table 4 gives the various conversions and selectivities.

TABLE 3

| Stream No. Component | 2 Mols/hr | 2 Mol % | 3 Mols/hr | 3 Mol % | 7 Mols/hr | 7 Mol % |
|---|---|---|---|---|---|---|
| n-butane | 54.331 | 1.9200 | 9.78 | 0.3391 | 9.78 | 0.3621 |
| iso-butane | 2.264 | 0.0800 |  | 0.0000 |  | 0.0000 |
| MAN |  |  | 32.82 | 1.1380 |  |  |
| CO |  |  | 33.08 | 1.1470 | 33.08 | 1.2247 |
| CO$_2$ |  |  | 23.63 | 0.8193 | 23.63 | 0.8748 |
| O$_2$ | 757.460 | 26.7681 | 567.79 | 19.6878 | 567.79 | 21.0216 |
| N$_2$ | 1947.747 | 68.8319 | 1947.85 | 67.5409 | 1947.85 | 72.1164 |
| H$_2$O | 67.913 | 2.4000 | 269.01 | 9.3279 | 118.85 | 4.4004 |
| Total | 2829.715 | 100 | 2883.95 | 100 | 2700.98 | 100 |

| Stream No. Component | 9 Mols/hr | 9 Mol % | 10 Mols/hr | 10 Mol % | 14 Mols/hr | 14 Mol % |
|---|---|---|---|---|---|---|
| n-butane | 44.46 | 96.0000 | 9.56 | 0.3413 | 9.56 | 0.3583 |
| iso-butane | 1.85 | 4.0000 |  |  |  |  |
| MAN |  |  | 30.92 | 1.1034 |  |  |
| CO |  |  | 68.17 | 2.4330 | 68.17 | 2.5538 |
| CO$_2$ |  |  | 48.69 | 1.7379 | 48.69 | 1.8241 |
| O$_2$ |  |  | 381.22 | 13.6054 | 381.22 | 14.2805 |
| N$_2$ |  |  | 1948.29 | 69.5333 | 1948.29 | 72.9634 |
| H$_2$O |  |  | 315.10 | 11.2456 | 213.56 | 8.0000 |
| Total | 46.34 | 100 | 2801.95 | 100 | 2669.50 | 100 |

TABLE 4

Basis Production of 63.74 mols/hr MAN
(equivalent to 6250 kg/hr of Product MAN)

|  | REACTOR 1 | REACTOR 2 | OVERALL FOR THE PLANT |
|---|---|---|---|
| Total n-butane Mol % | 2.00 | 2.00 | 3.56 |
| N-butane Purity % | 96.00 | 96.70 | 96.00 |
| Conc. n-butane | 1.92 | 1.93 | 3.42 |
| Conc. iso-butane | 0.08 | 0.06 | 0.14 |
| Conv. n-butane | 82.00 | 82.00 | 90.15 |
| Conv. iso-butane | 100.00 | 100.00 | 100.00 |
| Overall Conv. % | 82.72 | 82.59 | 90.54 |
| Selectivity % | 72.98 | 69.37 | 70.88 |
| Rx Yield, wt. % | 101.00 | 96.00 | 108.30 |

A comparison of Examples 1 and 2 demonstrates the improved yields which are achieved through practice of the invention wherein oxygen enriched air is fed to the first reactor.

I claim:

1. A process for the production of maleic anhydride from n-butane which comprises reacting a mixture of molecular oxygen containing gas and 0.5–3 vol % n-butane in a first reactor at conditions effective for the formation of maleic anhydride, scrubbing the reaction gas mixture from the first reactor to recover the maleic anhydride values from the remaining reaction gas mixture components, separating the scrubber liquid containing said maleic anhydride values, adding n-butane to said remaining reaction gas mixture components and reacting the resulting gas mixture in a second reactor at conditions effective for the formation of maleic anhydride.

2. The process of claim 1 wherein the reaction gas mixture from the first reactor is scrubbed with water.

3. The process of claim 1 wherein the feed to the second reactor comprises 0.5–3 vol % n-butane.

4. The process of claim 1 wherein air enriched with oxygen is the molecular oxygen containing gas in the first reactor.

5. The process of claim 1 wherein both n-butane and molecular oxygen are added to said remaining reaction gas mixture components.

6. The process of claim 1 wherein the gas mixture from the second reactor, after separation of maleic anhydride, is further reacted in a subsequent reactor after addition of n-butane and optionally molecular oxygen.

* * * * *